United States Patent
Sellergren et al.

(10) Patent No.: US 9,035,025 B2
(45) Date of Patent: May 19, 2015

(54) MOLECULARLY IMPRINTED SURFACES USING SURFACE-BOUND PEPTIDES

(75) Inventors: Börje Sellergren, Schwerte (DE); Maria Magdalena Titirici, Dortmund (DE); Andrew J. Hall, Dortmund (DE)

(73) Assignee: MIP Technologies AB (SE)

( * ) Notice: Subject to any disclaimer, the term of this patent is extended or adjusted under 35 U.S.C. 154(b) by 1320 days.

(21) Appl. No.: 10/707,990

(22) Filed: Jan. 30, 2004

(65) Prior Publication Data

US 2005/0171334 A1    Aug. 4, 2005

(51) Int. Cl.
*C07K 1/04* (2006.01)
*B01J 20/26* (2006.01)
*C07H 21/04* (2006.01)
*C07K 1/107* (2006.01)
*B01D 15/38* (2006.01)

(52) U.S. Cl.
CPC ............. *B01J 20/26* (2013.01); *B01D 15/3852* (2013.01); *B01J 20/268* (2013.01); *C07H 21/04* (2013.01); *C07K 1/04* (2013.01); *C07K 1/1077* (2013.01)

(58) Field of Classification Search
CPC ........... A61K 38/07; C07K 1/00; C07B 63/00
See application file for complete search history.

(56) References Cited

U.S. PATENT DOCUMENTS

| | | | | |
|---|---|---|---|---|
| 4,960,762 | A * | 10/1990 | Sellergren et al. | 514/57 |
| 5,872,198 | A * | 2/1999 | Mosbach et al. | 526/201 |
| 5,994,110 | A * | 11/1999 | Mosbach et al. | 435/173.1 |
| 6,444,321 | B1 | 9/2002 | Arnebrant et al. | 428/420 |
| 6,489,418 | B1 * | 12/2002 | Mosbach | 526/238.1 |
| 6,759,488 | B1 * | 7/2004 | Sellergren et al. | 526/67 |
| 6,870,021 | B2 * | 3/2005 | Sellergren et al. | 526/302 |
| 2004/0063159 | A1 * | 4/2004 | Mosbach et al. | 435/7.1 |

FOREIGN PATENT DOCUMENTS

| | | |
|---|---|---|
| WO | WO 01/32760 | 5/2001 |
| WO | WO 01/61354 | 8/2001 |

OTHER PUBLICATIONS

H. Kempe and M. Kempe. Novel Method for the Synthesis of Molecularly Imprinted Polymer Bead Libraries. Macromol. rapid. Commun. (2004) 25, pp. 315-320. Published online Jan. 2, 2004.*
Kempe, Maria, Oxytocin receptor Mimetics prepared by molecular imprinting, Letters in Peptide Science. 7: 27-33, (2000).*
Bratanova and Petkov, Glycine flanked by hydrophobic bulky amino acid residues as minimal sequence for effective subtilisin catalysis, Biochem. J. 248, 957-960 (1987).*
Kempe, Oxytocin receptor Mimetics prepared by molecular imprinting, Letters in Peptide Science. 7: 27-33, 2000.*
Bratove and Petkov, Glycine flanked by hydrophobic bulky amino acid residues as minimal sequence for effective subtilisin catalysis, Biochem. J. 248, 957-960 (1987.*
A. Rachkov, N. Minoura, Towards molecularly imprinted polymers selective to peptides and proteins. The epitope approach, Biochimica et Biophysica Acta 1544 pp. 255-266 (2001).*
Kempe, Oxytocin receptor mimetics prepared by molecular imprinting, Letters in Peptide Science, 7: 27-33, 2000.*
Nielsen et. al., Synthetic Methods for the Implementation of Encoded Combinatorial Chemistry, J. Am. Chern. Soc.vol. 115, 9812-9813, 1993.*
Guerrini et. al. Structure-activity Relationships of nociceptin and related peptides: comparison with dynorphin A, Peptides, vol. 21, 923-933, 2000.*
Chemical Book, http://www.chemicalbook.com/ChemicalProductProperty_EN_CB5704273.htm, last visited Jun. 23, 2013.*
Shi et. al. Template Imprinted nanostructured surfaces for protein recognition, Nature , vol. 398 , Apr. 15, 1999.*
Titirici et al., Heirarchical imprinting using crude peptide solid phase synthesis products as templates; Chem. Mater.; 2003; 15(4) pp. 822-824.

* cited by examiner

*Primary Examiner* — James H Alstrum Acevedo
*Assistant Examiner* — Jeanette Lieb
(74) *Attorney, Agent, or Firm* — Schwegman Lundberg & Woessner, P.A.

(57) ABSTRACT

A method of producing a molecularly-imprinted material comprises synthesizing a peptide, oligosaccharide or oligonucleotide on a disposable surface modified support to produce a support surface-attached peptide, oligosaccharide or oligonucleotide, providing a selected monomer mixture, contacting the monomer mixture with the support surface-attached peptide, oligosaccharide or oligonucleotide, initiating polymerisation or at least one crosslinking reaction, dissolving or degrading the support surface-attached peptide, oligosaccharide or oligonucleotide and support, and obtaining molecularly imprinted material.

9 Claims, 5 Drawing Sheets

SEQUENCE LISTING

```
<160> NUMBER OF SEQ ID NOS: 1

<210> SEQ ID NO 1
<211> LENGTH: 4
<212> TYPE: PRT
<213> ORGANISM: Artificial
<220> FEATURE:
<223> OTHER INFORMATION: Source: chemically synthesized

<400> SEQUENCE: 1

Phe Gly Gly Phe
1
```

MOLECULARLY IMPRINTED SURFACES USING SURFACE-BOUND PEPTIDES

BACKGROUND OF INVENTION

1. Field of the Invention

The invention relates to a method for the synthesis of materials in various formats containing surface-confined binding sites for solid phase synthesis products (e.g. peptides, oligonucleotides, oligosaccharides).

2. Background of the Invention

Molecular imprinting (G. Wulff, Angew. Chem., Int. Ed. Engl. 34 (1995) 1812-32) has emerged as a key technology in analytical and separation sciences (B. Sellergren (Ed.), Techniques and instrumentation in analytical chemistry, Vol. 23, Elsevier Science B.V., Amsterdam 2001; L. I.

Andersson, J. Chromatogr., B: Biomed. Sci. Appl. 745 (2000) 3-13; K. Haupt, K. Mosbach, Chem. Rev. 100 (2000) 2495-2504). The name refers to the synthesis of cross-linked polymers in the presence of templates, which may be small molecules, biological macromolecules, micro-organisms or crystals (B. Sellergren, Angew. Chem. Int. Ed. 39 (2000) 1031-1037).

The beauty of the molecular imprinting concept lies in its inherent simplicity. Functional monomers and the template to be imprinted form solution complexes which are subsequently incorporated into a cross-linked matrix upon polymerisation. Removal of the template leaves behind sites with a precise geometry and orientation of functional groups, allowing subsequent recognition of the template or a structurally-related compound. The molecularly imprinted polymer (MIP) thus created contains nanometer-sized binding sites in addition to larger sized pores (B. Sellergren, K. J. Shea, J. Chromatogr. 635 (1993) 31). Therefore, for guest molecules to access the host binding site they must penetrate pores, the size of which are difficult to control independently from the generation of the imprinted site. One way to decouple these processes is to immobilize the template on the surface of porous, disposable solids that act as molds to create a desired porosity (E. Yilmaz, K. Haupt, K. Mosbach, Angew. Chem., Int. Ed. 39 (2000) 2115-2118; M. M. Titirici, A. J. Hall, B. Sellergren, Chem. Mater. 14 (2002) 21-23).

In this way, the pore system is determined by the solid mold regardless of the conditions used to generate the imprinted sites. In addition, all imprinted sites are confined to the pore wall surface of the resulting material. Thus, access to these sites can be controlled by the porosity of the solid mold which may, in turn, allow substructures of larger target molecules to be recognised by the surface exposed sites. So far the feasibility of this approach has been demonstrated in the imprinting of small molecules, i.e. nucleotide bases (M. M. Titirici, A. J. Hall, B. Sellergren, Chem. Mater. 14 (2002) 21-23) and small drugs (E. Yilmaz, K. Haupt, K. Mosbach, Angew. Chem., Int. Ed. 39 (2000) 2115-2118).

Despite these advances, a thorough evaluation of the benefits of confining the sites to the pore wall surface is still lacking. Particularly lacking is any suggestion of how to use this concept for the development of affinity phases for the separation of biological macromolecules, e.g. peptides, proteins, oligo- or poly-nucleotides or oligo- or poly-saccharides (see for instance B. R. Hart, K. J. Shea, J. Am. Chem. Soc. 123 (2001) 2072-2073; A. Rachkov, N. Minoura, Biochim. Biophys. Acta 1544 (2001) 255-266 for other examples of imprinted peptide receptors). In this regard, the format would allow a more efficient exploitation of the epitope approach, recently introduced by Rachkov and Minoura (A. Rachkov, N. Minoura, Biochim. Biophys. Acta 1544 (2001) 255-266).

In this approach, a smaller peptide corresponding to a unique amino acid sequence of a target protein is used as template in order to generate a site that can subsequently selectively bind the larger target molecule. This requires that the site is associated with the accessible surface of larger pores capable of accommodating the larger protein.

SUMMARY OF INVENTION

It is therefore an object of the present invention to provide a new method for producing a molecularly-imprinted material.

According to a first embodiment of the invention, a method of producing a molecularly-imprinted material is provided which comprises synthesizing a peptide, oligosaccharide or oligonucleotide on a disposable surface modified support to produce a support surface-attached peptide, oligosaccharide or oligonucleotide, providing a selected monomer mixture, contacting the monomer mixture with the support surface-attached peptide, oligosaccharide or oligonucleotide, initiating polymerisation or at least one crosslinking reaction, dissolving or degrading the support surface-attached peptide, oligosaccharide or oligonucleotide and support, and obtaining molecularly imprinted material.

The peptide synthesized on the surface of the support could be a peptide epitope. The polymerization or crosslinking reaction may be conducted with the aid of crosslinking agents, heat, or ultraviolet irradiation. The peptide, oligosaccharide or oligonucleotide may be FMOC-Phe-Gly-Si, H-Phe-Gly-Si, FMOC-Phe-Si, BOC-Gly-Si, H-Gly-Si, FMOC-Phe-Gly-OH, FMOC-Phe-OH, BOC-Phe-OH, H-Phe-pNA, H-Phe-O-Me, H-Phe-OtBu, BOC-Gly-OH, H-Phe-Gly-NH$_2$, H-Phe-Gly-Gly-Phe-OH (SEQ ID NO:1), FMOC-Phe-OH, H-Gly-Phe-OH, or Nociceptin. The disposable surface activated support may be silane-modified silica or controlled pore glass. The monomer mixture may comprise monomers such as styrene/divinyl benzene, methacrylates, acrylates, acrylamides, methacrylamides or combinations thereof.

Another embodiment of the invention contemplates a method of using a molecularly-imprinted material which comprises producing a molecularly-imprinted material according to the invention as described above and using that molecularly-imprinted material as an affinity phase for the separation of biological macromolecules and oligomers. The biological macromolecules or oligomers may be peptides, polypeptides, oligopeptides, proteins, nucleic acids, oligonucleotides, polynucleotides, saccharides, oligosaccharides, or polysaccharides.

According to a further embodiment of the present invention, a chromatographic stationary phase is provided which comprises a molecularly imprinted material produced according to the first embodiment of the invention described above, where the peptide, oligosaccharide or oligonucleotide may be one of FMOC-Phe-Gly-Si, H-Phe-Gly-Si, FMOC-Phe-Si, BOC-Gly-Si, H-Gly-Si, FMOC-Phe-Gly-OH, FMOC-Phe-OH, BOC-Phe-OH, H-Phe-pNA, H-Phe-O-Me, H-Phe-OtBu, BOC-Gly-OH, H-Phe-Gly-NH$_2$, H-Phe-Gly-Gly-Phe-OH (SEQ ID NO:1), FMOC-Phe-OH, and H-Gly-Phe-OH.

DETAILED DESCRIPTION

Figure 1:
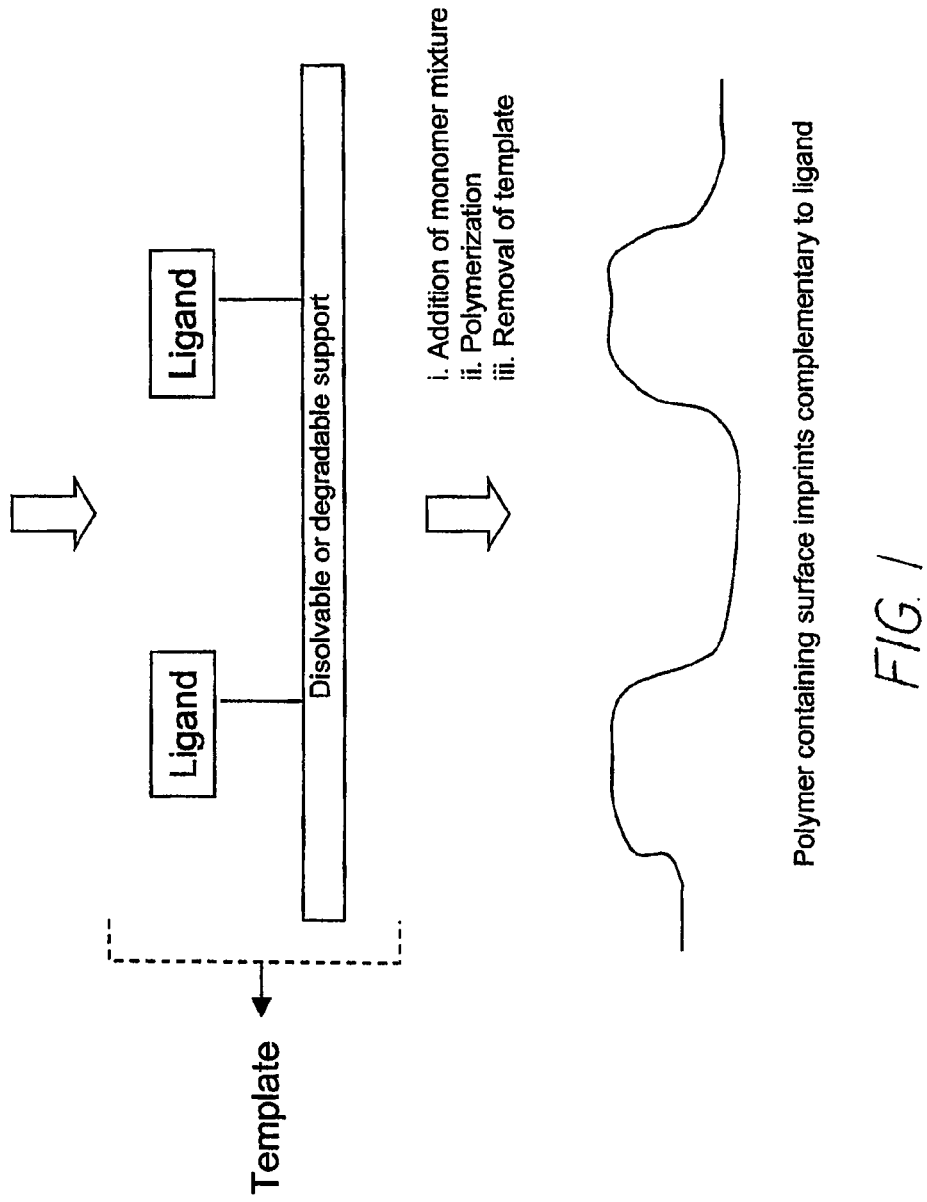
FIG. 1 schematically represents a method of producing a molecularly imprinted material according to the present invention, wherein the ligand could be a peptide, oligosaccharide or oligonucleotide.

The invention refers to the use of crude products resulting from solid phase synthesis as porous mold and molecular templates in hierarchical imprinting (FIG. 1). For instance after the solid phase synthesis of a peptide corresponding to a particular epitope of a given target peptide or protein, the crude support-bound peptide can serve as epitope templates to generate surface confined sites with affinity for the larger peptide or protein target. One requirement in this approach is that the peptide is synthesized on a disposable support which can be based on silica, another inorganic oxide, a soluble or degradable linear or crosslinked polymer or any modified form of such materials.

Instead of modified silica, the mold can also be made of controlled pore glass (CPG) which allows the direct use of the synthesis products resulting from solid phase DNA or oligonucleotide synthesis to be used as templates. Thus oligonucleotide-modified CPG can be used to create materials with affinity for the same oligonucleotides, or DNA or RNA containing sequences corresponding to the template. All these possibilities are depicted in FIG. 1.

The invention will be described in more detail with reference to a number of non-limiting examples. The invention refers to a material containing surface-confined binding sites for oligomers or polymers, a method for its" fabrication and use, for example, in chromatography, for separations, in chemical sensors, in drug discovery, in selective sample enrichment, in molecular recognition as stationary phase in capillaries, or in catalysis. As further detailed below, the inventive method comprises several stages or steps. In one embodiment those steps include attachment of a link aminoacid molecule to a modified or activated support surface, in-situ synthesis of the template molecule (typically a di- or poly-peptide corresponding to a protein epitope), polymerization of a suitable monomer mixture in contact with the immobilised template, and removal of the template and support by a dissolution or degradation method, to give the desired molecularly imprinted material (typically polymer containing surface imprints complementary to the template molecule(s)).

Therefore, one important contribution made by the present invention is the ability to synthesize a polypeptide template that can be further built up, step-by-step, in-situ at the surface of the support. This ability for in-situ synthesis of the template molecule allows for the possibility to control orientation and 3-D stereochemistry of the final template molecule, such that the final imprint cavities on the molecularly imprinted material are more well-defined and homogeneous. Examples of how the invention is applied to the synthesis of peptide selective materials in various formats are given below.

Figure 2:
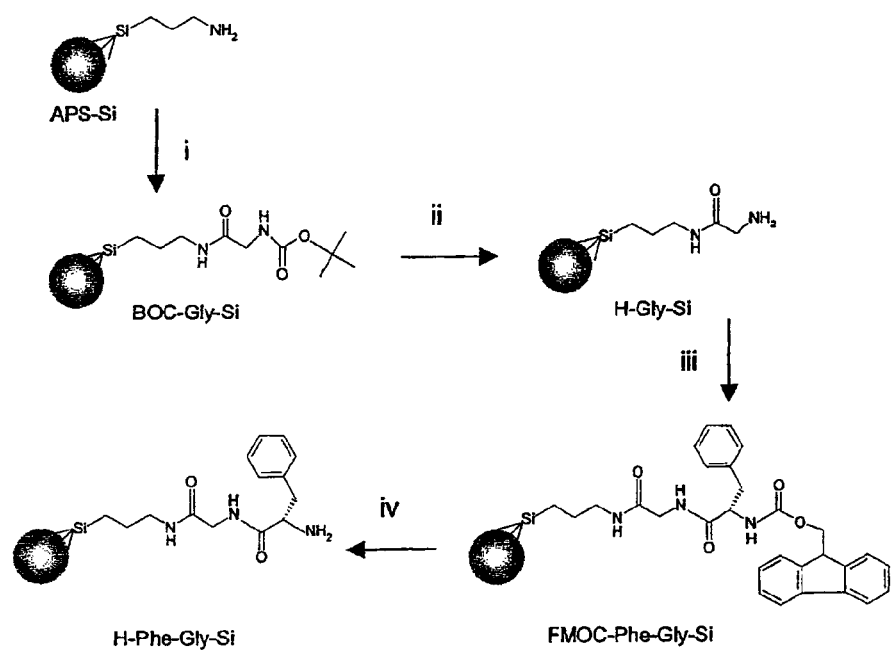
FIG. 2 illustrates the synthesis of a peptide on the surface of a disposable support.
Figure 3:
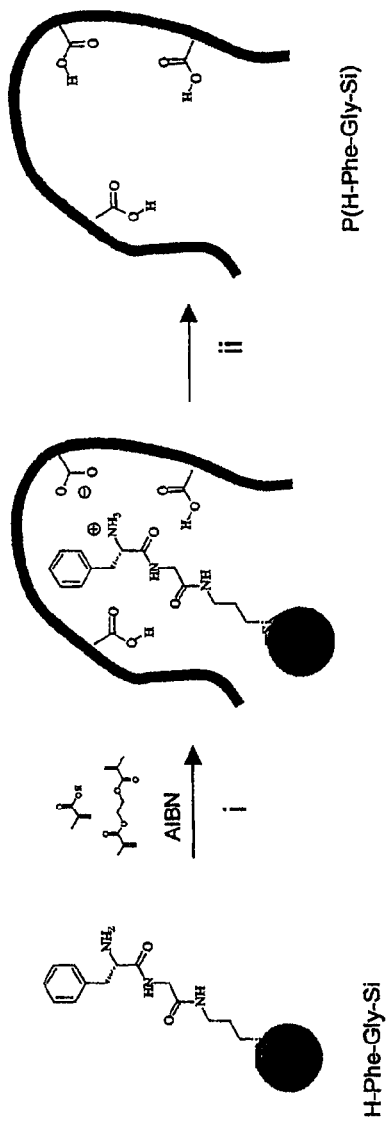
FIG. 3 illustrates the generation of a molecularly imprinted material using a surface-immobilized peptide.

The material is prepared by first synthesising a peptide on the surface of a disposable support which can be porous silica as depicted in FIG. 2. The immobilised peptide is then used as a template for the generation of a hierarchically-imprinted material (FIG. 3). Here the surface of the immobilized peptide is first brought in contact with the monomer mixture used to create the imprints. For instance, it is possible to prepare the polymers using monomers such as those based on styrene/divinylbenzene, methacrylates, acrylates, acrylamides or combinations of these monomers. After polymerization, the support or mold is removed by dissolution or degradation and the peptide template isolated for reuse. The polymer can then be used for rebinding of the peptide template or a larger peptide or protein containing the template amino acid sequence.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention. Materials, the synthesis of which are not specifically described, are either commercially available or can be prepared using methods well known to those of skill in the art.

EXAMPLE 1

Synthesis of the Peptide or Peptide Epitope

Using aminopropyl silica with an average pore size of 11.5 nm as a common support material, peptides were synthesised using standard Merrifield chemistry. Thus, in the first step, BOC-Gly-OH was coupled through DCC catalysed amide bond formation. After deprotection, FMOC-Phe-OH was coupled in order to obtain the N-protected or, after deprotection, free dipeptide coupled through its carboxy terminus to the support surface. Each intermediate was characterised by carbon and nitrogen microanalysis, infrared spectroscopy and fluorescence microscopy (Table 1). From the change in carbon and nitrogen content, with reference to the starting material, the area density ($D_S$) of the coupled ligand could be estimated together with the associated coupling yield. Assuming a maximum area density of 8 μmol/m², APS occupies about 50% of the available sites. The coupling of BOC-Gly-OH appeared quantitative and was accompanied by the appearance of strong characteristic amide bands in the IR spectrum. The following steps appeared to occur in high yield and could, aside from the amide characteristic bands in the IR spectra, be followed visually by fluorescence microscopy. Thus, coupling of FMOC-Phe-OH was accompanied by a strong particle fluorescence which disappeared completely upon deprotection. The area density of the final coupling products was found to be in the range 1-2 μmol/m².

EXAMPLE 2

Synthesis of the Peptide Imprinted Material

Subsequent to the template synthesis, the pores of the immobilized amino acid or peptide templates were filled with a mixture of MAA, EDMA and azoinitiator (AIBN) (FIG. 3). The molar ratio: MAA/EDMA was 4/20.

This mixture was thereafter thermally cured at 60° C. Dissolution of the silica mold by treatment with a solution of $NH_4HF_2$ (aq) resulted in organic polymer beads with a size and morphology reflecting those of the original silica mold (Table 1). In addition, the immobilized amino acids and peptides leave behind surface imprints leading to preferential retention of the template peptide when assessing the materials as stationary phases in chromatography. The extent of removal of the silica and peptide template was revealed by the elemental analysis of the final polymer product. The carbon and nitrogen contents indicated that more than 95% of the template was removed upon the fluoride treatment. As a control FMOC-Phe//Si was prepared using APS-Si as a pore template and FMOC-Phe-OH dissolved in the monomer mixture prior to pore filling. The molar ratio: template/MAA/EDMA was 1/4/20.

The polymers were also characterised by recording their nitrogen sorption isotherms. S=surface area determined using the BET model, $V_p$=the total volume of pores with diameter less than 109 nm according to Gurvitch and $d_p$=the average pore diameter according to the MJH model.

EXAMPLE 3

Figure 4A:
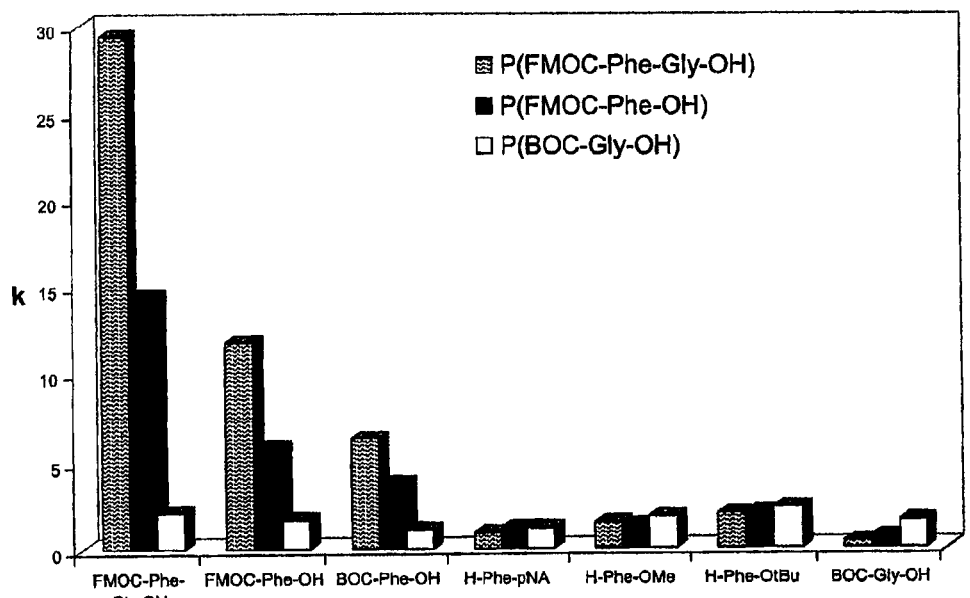
FIG. 4A shows assessment results of several dipeptide imprinted materials as stationary phases in chromatography.
Figure 4B:
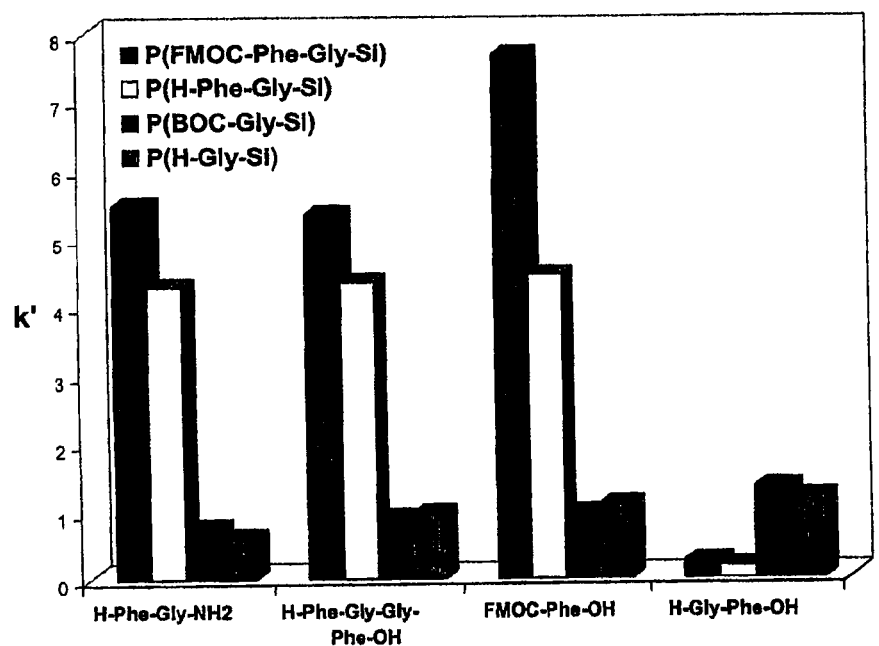
FIG. 4B shows assessment results of several dipeptide imprinted materials as stationary phases in chromatography.
Figure 4C:
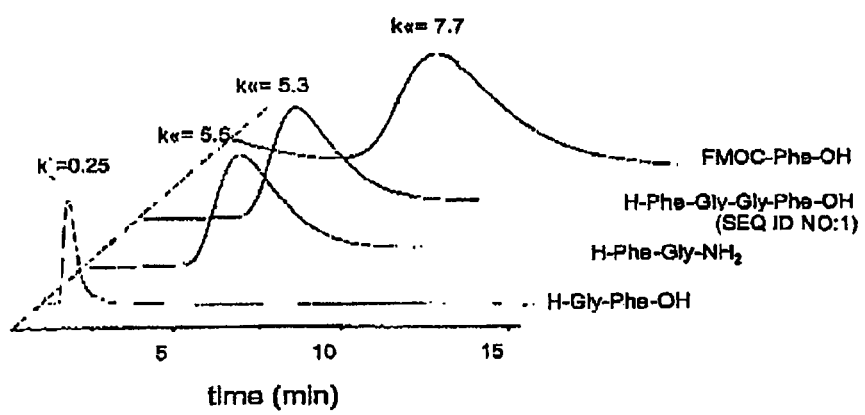
FIG. 4C shows assessment results of several dipeptide imprinted materials as stationary phases in chromatography.

Application of Peptide Selective Phases as Chromatographic Stationary Phases The polymers were subsequently assessed as stationary phases in chromatography. The dipeptide imprinted materials were focused upon. As seen in FIG. 4A, FMOC-Phe-Gly-OH is about two times more strongly retained on P(FMOC-Phe-Gly-Si) than on P(FMOC-Phe-Si) and about 15 times more strongly on P(FMOC-Phe-Gly-Si) than on P(BOC-Gly-Si). The retention behaviour in aqueous mobile phases is crucial for the application of these phases to biological samples. Water was therefore added to the mobile phase (buffered with 1% HOAc) in increments of 5%. The retention of different peptides on the dipeptide imprinted materials (P(FMOC-Phe-Gly-Si) and P(H-Phe-Gly-Si)) was compared using the glycine imprinted materials (P(BOC-Gly-Si and P(H-Gly-Si)) as controls. With 5% water a pronounced selectivity for peptides containing the imprinted dipeptide motif is seen (FIGS. 4B, 4C). This also included larger peptides containing the H-Phe-Gly motif as N-terminus. Thus, H-Phe-Gly-Gly-Phe-OH (SEQ ID NO:1) is similarly retained to H-Phe-Gly-NH$_2$, with a retention factor, k', of almost 6 on P(FMOC-Phe-Gly-Si). Also, the larger, 17 amino acid long, oligopeptide nociceptin that contained the Phe-Gly as amino terminus was selectively retained on P(H-Phe-Gly-Si). Additional strong evidence for the presence of peptide discriminating sites is provided by the retention behaviour of the dipeptide H-Gly-Phe-OH with the inverse amino acid sequence. In contrast to the other dipeptides, this is most strongly retained on the materials imprinted with the nearest complement used in this study, namely H-Gly-Si and BOC-Gly-Si.

---

---

The invention claimed is:

1. A method of producing a hierarchical molecularly-imprinted material, comprising:
    (a) synthesizing at least one peptide corresponding to an epitope of a target peptide or target protein by attaching a first amino acid to modified surfaces of the pores of a disposable surface-modified porous support, followed by attaching one or more amino acids to said first amino acid to produce said at least one peptide attached to said surfaces;
    (b) providing a selected monomer mixture;
    (c) contacting said monomer mixture with said support surface-attached peptide so that the monomer mixture enters the pores of the porous support;
    (d) initiating polymerisation or at least one crosslinking reaction of said monomer mixture to yield a polymer; and
    (e) dissolving or degrading said at least one support surface-attached peptide and said support;
    to provide a polymer material comprising a hierarchical molecular imprint of the epitope synthesized in step (a) and the porous support,
        wherein the epitope is a peptide that corresponds to only part of the target peptide or protein.

2. A method according to claim 1, wherein said target peptide is a dipeptide or oligopeptide.

3. A method according to claim 1, wherein step (d) is conducted with the aid of at least one factor consisting of crosslinking agents, heat, and ultraviolet irradiation.

4. A method according to claim 1, wherein said epitope of a target peptide is selected from the group consisting of FMOC-Phe-Gly-Si, H-Phe-Gly-Si, FMOC-Phe-Gly-OH, H-Phe-Gly-NH$_2$, H-Phe-Gly-Gly-Phe-OH (SEQ ID NO:1), and H-Gly-Phe-OH.

5. A method according to claim 1, wherein said disposable surface modified support is modified silica or controlled pore glass (CPG).

6. A method according to claim 1, wherein said monomer mixture comprises monomers selected from the group consisting of styrene/divinyl benzene, methacrylates, acrylates, acrylamides, methacrylamides and combinations thereof.

7. A method of using a molecularly-imprinted material, comprising:
    producing a molecularly-imprinted material according to claim 1; and
    using said molecularly-imprinted material as an affinity phase for the separation of biological macromolecules or oligomers.

8. A method according to claim 7, wherein said biological macromolecules or oligomers are selected from the group consisting of peptides, polypeptides, oligopeptides, proteins, nucleic acids, oligonucleotides, polynucleotides, saccharides, oligosaccharides, and polysaccharides.

9. A chromatographic stationary phase, comprising a molecularly imprinted material produced according to claim 1, wherein said peptide, oligosaccharide or oligonucleotide of step (c) is selected from the group consisting of FMOC-Phe-Gly-Si, H-Phe-Gly-Si, FMOC-Phe-Gly-OH, H-Phe-Gly-NH$_2$, H-Phe-Gly-Gly-Phe-OH (SEQ ID NO:1), and H-Gly-Phe-OH.

\* \* \* \* \*